US006238650B1

(12) United States Patent
Lapidot et al.

(10) Patent No.: US 6,238,650 B1
(45) Date of Patent: *May 29, 2001

(54) SUNSCREEN COMPOSITION CONTAINING SOL-GEL MICROCAPSULES

(75) Inventors: Noa Lapidot, Mevasseret Zion; Shlomo Magdassi, Jerusalem; David Avnir, Jerusalem; Claudio Rottman, Jerusalem; Orit Gans, Efraim; Alon Seri-Levy, Rehovot, all of (IL)

(73) Assignee: Sol-Gel Technologies Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,828

(22) Filed: May 26, 1999

(51) Int. Cl.$^7$ ................... A61K 7/42; A61K 7/44; A61K 7/06; A61K 9/48; A61K 9/66
(52) U.S. Cl. ............... 424/59; 424/60; 424/70.9; 424/401; 424/451; 424/455; 424/489; 424/490; 514/962
(58) Field of Search ................... 424/59, 60, 401, 424/451, 455, 489, 490, 70.9; 514/962

(56) References Cited

U.S. PATENT DOCUMENTS

| 4,129,645 | * | 12/1978 | Barnett et al. | 424/60 |
|---|---|---|---|---|
| 5,200,334 | * | 4/1993 | Dunn et al. | 435/182 |
| 5,387,622 | * | 2/1995 | Yamamoto | 523/102 |
| 5,607,664 | * | 3/1997 | Ascione et al. | 424/59 |
| 5,733,531 | * | 3/1998 | Mitchnick et al. | 424/59 |
| 5,739,020 | * | 4/1998 | Pope | 435/176 |
| 5,876,699 | * | 3/1999 | DiSomma et al. | 424/59 |

FOREIGN PATENT DOCUMENTS

98/31333 * 7/1998 (WO).

OTHER PUBLICATIONS

"Contact and photocontact sensitivity to sunscreens—review of a 17–year experience and of the literature", S. Schauder and H. Ippen, European UV Sunfilters, Conference Proceedings, Paris 17–18, Nov. 1998, p. 14.

"Sunlight–induced mutagenicity of a common sunscreen ingredient", Knowland et al, FEBS Letters, 324, 309–313, 1993.

"Photosensitization of Guanine–Specific DNA Damage by 2–Phenylbenzimidazole and the Sunscreen Agent 2–Phenylbenzimidazole–5–sulfonic Acid", C. Stevenson and R.J.H. Davies, Chem. Res. Toxicol, 12, 38–45, 1999.

"Photocatalytic Degradation of Organic Contaminants: Halophenols and Related Model Compounds", U. Stafford, K.A. Gray and P.V. Kamat, Heterogeneous Chem. Rev. 3, 77–104, 1996.

"Uric acid photo–oxidation assay: in vitro comparison of sunscreening agents", W. C. Dunlap et al, Int. J. Cosmetic. Sci. 20, 1–18, 1998.

"Sun Protection—The influencing Factors in Creating Effective Products" W. Johncock, Mar. 1999. London.

* cited by examiner

Primary Examiner—Shelley A. Dodson
Assistant Examiner—Marina Lamm
(74) Attorney, Agent, or Firm—Lowe Hauptman Gilman & Berner, LLP

(57) ABSTRACT

The present invention generally relates to safe and stable sunscreen compositions comprising of at least one sunscreen active ingredient in the form of an inert sol-gel microcapsules encapsulating ultraviolet absorbing compounds in any acceptable cosmetic vehicle. The composition according to the present invention can comprise several ultraviolet absorbers that may be encapsulated in the same sol-gel microcapsule or in different capsules. The encapsulation of the ultraviolet absorbers reduces or even prevents the contact between the sunscreen compounds and the human tissue, thus reducing various adverse effects that are associated with the use of sunscreens, such as photoallergy and phototoxicity, and makes the composition safer for use. The encapsulation also reduces or even prevents cross reactivity between the sunscreen compounds and the packaging material and between the sunscreen compounds and any other component present in the composition, thus enhance the compositions stability. The hydophobicity/hydrophilicity character of the sol-gel microcapsules can be controlled by selecting suitable sol-gel precursors and suitable reaction conditions and can be chosen to be compatible with the cosmetic vehicle to be used in the sunscreen composition, thus, the present invention facilitates an easy incorporation of the composite sol-gel encapsulated sunscreen in all types of cosmetic vehicles including oil free compositions, with no necessary steps of heating or high shear forces. The sunscreen compositions of the present invention can comprise any acceptable UVA and/or UVB absorbing compounds at any desired ratio to obtain a desired accumulative ultraviolet screening spectrum.

37 Claims, 1 Drawing Sheet

SUNSCREEN COMPOSITION CONTAINING SOL-GEL MICROCAPSULES

FIELD OF THE INVENTION

The present invention generally relates to safe and stable sunscreen compositions. More specifically the present invention relates to a sunscreen composition comprising of at least one sunscreen active ingredient in the form of inert sol-gel microcapsules encapsulating UVB and/or UVA sunscreen compounds (ultraviolet absorbers), in any acceptable cosmetic vehicle. The composition according to the present invention can comprise several ultraviolet absorbers that may be encapsulated in the same sol-gel microcapsule or in different capsules. The encapsulation of the ultraviolet absorbers makes the composition safer for use, since the encapsulating sol-gel material forms a barrier that reduces or even prevents contact between the sunscreen compounds and human tissue. Hence, various adverse effects that are associated with the use of sunscreens, such as photoallergy and phototoxicity are prevented. Furthermore, the encapsulation reduces or even prevents cross reactivity between different sunscreen compounds when more than one such compound is present in the composition, between the sunscreen compounds and the packaging material and between the sunscreen compounds and any other component present in the composition. The present invention facilitates an easy incorporation of the composite sol-gel encapsulated sunscreen in all types of cosmetic vehicles including oil free compositions, with no necessary steps of heating or high shear forces.

BACKGROUND OF THE INVENTION

Sunscreens compositions are chemical compositions, which are usually applied topically to skin and hair in order to protect them from the damaging effects of the sun's radiation, especially against ultraviolet (UV) radiation.

The damaging effects of sunlight exposure on skin and hair are well documented. These effects include increased incidence of skin carcinogenesis, pigmentation, anomalies and precancerous lesions such as actinic keratosis, melanoma and nonmelanoma skin cancers, as well as accelerated skin aging and undesirable changes in hair quality. In recent years, a growing number of studies show that damage is caused not only by the UVB irradiation (290–320 nm), but also by UVA irradiation (320–400 nm).

The use of UV absorbing chemicals for human application is regulated by the health authorities. In the US and Australia sunscreens are regulated as over-the-counter (OTC) drugs, consequently introduction of new sunscreen active ingredients requires heavy investment of time and money. Most of the UV absorbing agents allowed for use are UVB absorbers. These include para amino benzoates, salicylates, cinnamates, anthranilate, camphors and miscellaneous chemicals. The number of UVA absorbers is more limited, with benzophenones (UVB and UVA absorber) and dibenzoylmethanes (UVA absorber) being the most widely used.

Some of the sunscreen active ingredients have been found to cause photoallergy and photosensitization reactions, encouraging the manufacturers to avoid using them. For example, growing public awareness to the photosensitization reactions of PABA and its derivatives has encouraged the use of PABA free products (see S. Schauder and H. Ippen, European UV Sunfilters, Conference Proceedings, Paris 17–18 November 1998, p. 14). The production of another sunscreen, 4-isopropyl dibenzoyl methane was ceased in 1993 due to the high number of photoallergy incidents reported for this active ingredient (Ibid). Moreover, some of the reported cases of adverse reactions to sunscreen active ingredients relate the adverse reactions to cross reactivity of several sunscreen ingredients, as in the case of cross sensitization between different cinnamate derivatives (Ibid). Moreover, several research groups have demonstrated the photoinduced DNA damage and phototoxicity of several sunscreen agents, including Padimate-O (Knowland et al, FEBS Letters, 324, 309–313, 1993), Phenylbenzimidazole sulfonic acid (C. Stevenson and R. J. H. Davies, Chem. Res. Toxicol, 12, 38–45, 1999). Physical sunscreens such as titanium dioxide are known to be photocatalysts capable of rupturing covalent bonds (U Stafford, K. A. Gray and P. V. Kamat, Heterogeneous Chem Rev. 3, 77–104, 1996), and have been shown to produce reactive oxygen species under illumination (W. C. Dunlap et al, Int. J. Cosmetic. Sci. 20, 1–18, 1998).

With the growing demand for higher SPF values and for broad-spectrum protection, manufacturers are forced to combine several active ingredients at increased concentrations (often the maximum permitted concentrations), hence the problem of cross reactivity between sunscreen active ingredients is becoming more severe. An example for cross reactivity effects is the photoinduced interaction between butyl methoxydibenzoylmethane (also known as 4,4'-methoxy-t-butyldibenzoylmethane or BMDBM), an excellent UVA absorber, with the most widely used UVB absorber octyl methoxycinnamate (R. M. Sayre et. al, $26^{th}$ Annual Meeting if the American Society for Photobiology, Abstr. No. SPM-A7). This cross reactivity contributes significantly to the photochemical instability of both the UVB and the UVA active ingredients. Another problem associated with BMDMB that presents a number of composition formulation problem, is its tendency to react with active methylene groups such as those present in formaldehyde releasing preservatives at temperatures above 30° C., thus restricting the use of such preservatives (W. Johncock, Sun Protection The Influencing Factors in Creating Effective Products, March 1999 London, March 1999 and references therein).

Another problem, associated with the use of high sunscreen compounds concentrations, is the tendency of some of these ingredients to crystallize at certain pH range, or if the amount of oil in the composition is not sufficient.

Yet, another problematic aspect in sunscreen products is the selection of packaging material. Liquid UVB filters permeate into various plastic packaging materials (polystyrene as one example), and consequently cause decomposition or coloration of the packaging materials. UV absorbing liquids are able to permeate polymers like polystyrene, low density polyethylene and polyethylene terphthalate. This can cause fracturing of the packaging material, unacceptable colouring of white packaging material with time, and assay problems such as ensuring that the proper content of active ingredients are in maintained upon storage.

In the present invention it has been found that if the sunscreen active ingredients are introduced into the cosmetic vehicle in the form of sol-gel encapsulated sunscreen, cross reactivity of sunscreen active ingredients, e.g. butyl methoxydibenzoylmethane and octyl methoxycinnamate, can be reduced or even prevented. The separate encapsulation of sunscreen active ingredients in the sol-gel derived capsules creates a barrier that prevents cross interactions between these active ingredients. Furthermore, the encapsulation of UV absorbing liquids in sol-gel derived capsules reduces the contact between these liquids and the packaging material.

Consequently, the problem of adverse reactions caused following permeation of the sunscreen active ingredients into the packaging material is diminished. Furthermore, the use of sol-gel encapsulated sunscreens facilitate the incorporation, in the same composition, of several components that are incompatible when simply dissolved in the composition, for example 2-phenyl benzimidizole-5-sulfonic acid with α or β hydroxy acids. The present invention also allows easy incorporation of solid sunscreen active ingredient or active ingredients that tend to precipitate in various compositions, since even in a situation that solid is formed, the crystals are confined within the sol-gel capsules, hence, a pleasant non gritty feel and efficient spreading are maintained. Yet another advantage of the present invention is the ability to control the hydrophilicity/hydrophobicity character by choosing a suitable sol-gel encapsulating material, thus the encapsulated sunscreen can be conveniently introduced into the composition.

It is an object of the present invention to provide safer sunscreen compositions by reducing or even preventing the contact of the light absorbing molecules (sunscreen compounds), or their possible light-induced degradation products, with human tissue.

It is another object of this invention to provide a stable and safer sunscreen composition by reducing or even preventing cross reactivity between various ingredients present in the same composition.

It is a further object of this invention to reduce or even to prevent the deleterious permeation of sunscreen active ingredient into plastic packaging materials which may result in fracturing of the packaging material, unacceptable colouring of white packaging material with time, and assay problems.

It is a further object of this invention to provide the formulator with an easy-to-use sunscreen active ingredients, which can be incorporated easily, without applying heat or high shear forces, in any cosmetically accepted vehicle.

Yet it is another object of the present invention to provide an easy incorporation of solid sunscreen active ingredient or of active ingredients that tend to precipitate, in various compositions, to thereby maintain a pleasant non gritty feel and efficient spreading.

The compositions revealed by this invention are of general nature, and the method according to which they are prepared is applicable to any sunscreen compounds currently used, as well as to sunscreen compounds that will be introduced in the future. It is also applicable for other compounds that are regularly used in cosmetic compositions. Furthermore, because of the easy incorporation of the sunscreen active ingredients and the ability to control their hydrophilicity/hydrophobicity character and the capsules size, the cosmetic vehicle to be used with the sunscreen active ingredients is not limited to any group and can be any cosmetically acceptable vehicle.

In the context of the present invention the term "sunscreen compound" refers to an ultraviolet (UVA and/or UVB) absorbing chemical that can be used in sunscreen composition.

In the context of the present invention the term "sol-gel microcapsule" relates to a core material which is coated by a sol-gel coating matrix.

In the context of the present invention the term "sunscreen active ingredient" refers to sol-gel microcapsules wherein the core material is a sunscreen compound.

SUMMARY OF THE INVENTION

The present invention relates to a sunscreen composition comprising as an active ingredient sol-gel derived microcapsules that encapsulate ultraviolet (UV) absorbing compounds and any cosmetically acceptable vehicle. The encapsulation of the UV absorbers forms a barrier between them and the human tissue, as well as between them and the other ingredients present in the formula and with the container in which the product is contained. The present invention further relates to sunscreen compositions in which cross reactivity between different sunscreen compounds, present in the same composition, is reduced or even prevented.

The sunscreen active ingredient in the form of sol-gel microcapsules, is prepared by the method disclosed in U.S. patent application Ser. No. 60/097,552. The size of the microcapsules obtained by this method can be controlled to the range $0.01–100\mu$, preferably $0.1–10\ \mu$, by selecting suitable reaction conditions. The hydrophobicity/hydrophilicity character of the sol-gel microcapsules can be controlled by selecting suitable sol-gel precursors and suitable reaction conditions and can be chosen to be compatible with the cosmetic vehicle to be used in the sunscreen composition, therefore said microcapsules can be incorporated easily into any acceptable cosmetic vehicle. The sunscreen active ingredient can be incorporated into the cosmetic vehicle in the form of an aqueous suspension of the sol-gel particles, or as a dried sol-gel powder. In a preferred embodiment of this invention, the sol-gel derived capsule materials consist of the encapsulated matter and silica or organically modified silica, in particular methyl modified silica.

The sunscreen compound can be selected from any acceptable UVA absorber or UVB absorber or combination thereof.

The compositions of the present invention can comprise a single active ingredient in the form of sol-gel microcapsules that encapsulate a single sunscreen compound or several sunscreen compounds together, or a combination of the active ingredients, to obtain a composition with the desired UV absorption spectrum. The concentration ratio of the active sunscreen ingredients present at the same composition is not limited and can be of any value. The sunscreen compositions according to the present invention can comprise about 1 to about 80 wt.%, in particular from about 10 to about 50 wt% (weight percent of the final composition), water suspension of sol-gel derived capsules, in any cosmetically acceptable vehicle, or can comprise about 1 to about 40 wt.%, in particular from about 5 to about 25 wt.% dry powder of sol-gel capsules, in any cosmetically acceptable vehicle.

The present invention further relates to the sol-gel microcapsules encapsulating sunscreen compound for use as a sunscreen active ingredient in sunscreen compositions. This sunscreen active ingredient can be added to the cosmetic compositions at the end of the composition process, without the application of heat or shear forces. However, such steps of composition information may be carried out if required for the purpose of formulating other constituents of the composition. The sunscreen active ingredient can be incorporated in any cosmetically acceptable oil-in-water or water-in-oil compositions; the final product may take the form of an oil, a gel, a solid stick, a lotion, a cream, a milk, an aerosol, a spray, a powder, a foam, a shampoo, a hair conditioner or lacquer or a make-up.

The compositions according to the present invention are of a general nature, and applicable to any sunscreen compounds currently used, as well as to compounds that will be introduced in the future. It is also applicable for other active ingredients that are regularly used in cosmetic compositions.

DETAILED DESCRIPTION OF THE INVENTION

Figure 1:
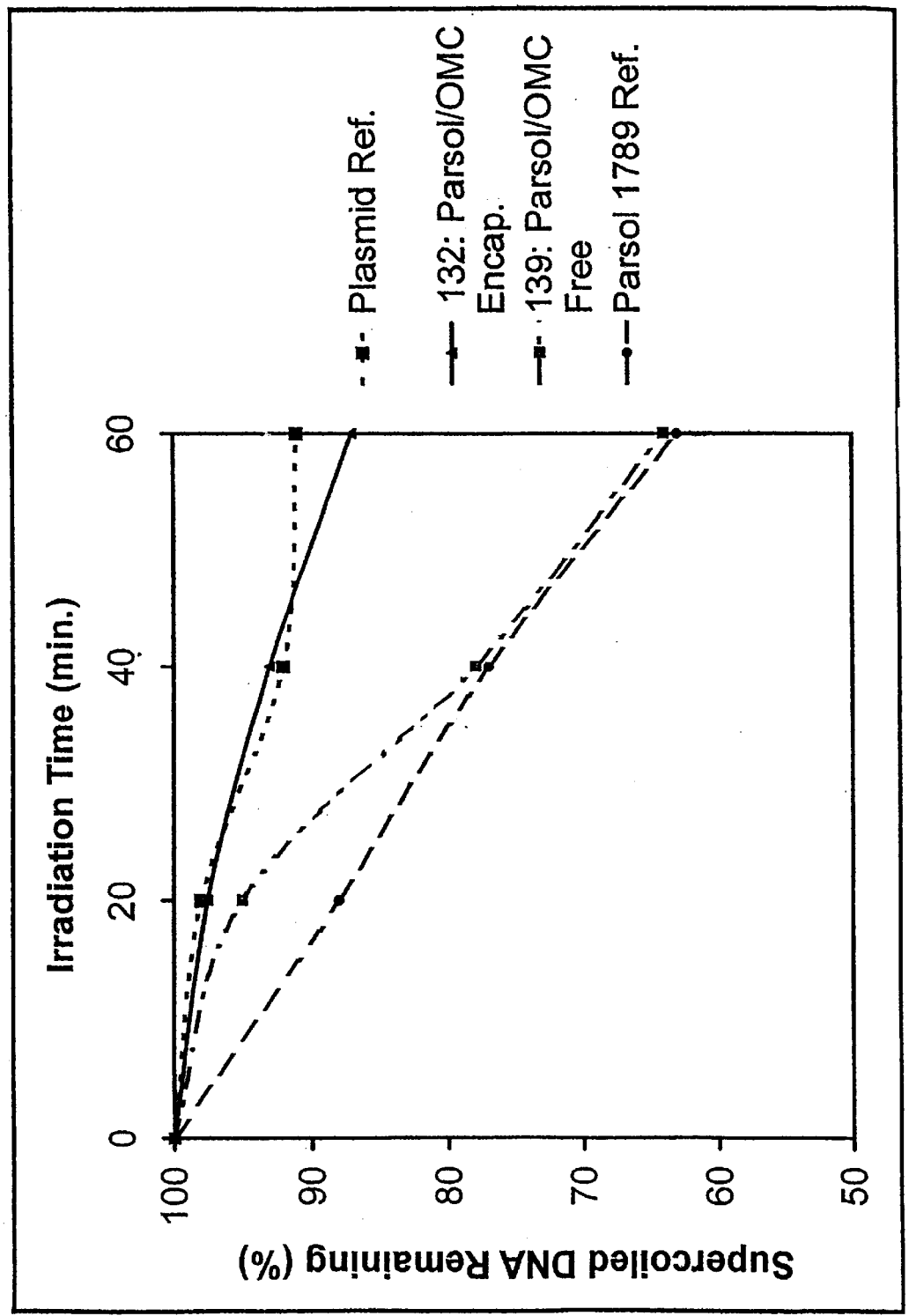
FIG. 1 is a graph of supercoiled DNA remaining as a function of irradiation time with respect to some samples.

The present invention relates to stable and safer sunscreen compositions in which the contact between the sunscreen compounds and the human tissue, and the reactivity between sunscreen compound and other components present in the composition are reduced or even prevented, by encapsulation of the sunscreen compound/s in a sol-gel derived microcapsules. The selection of the cosmetic vehicle to be used in the composition is not limited and can be any cosmetically acceptable vehicle. The encapsulated sunscreen compound/s can be incorporated into the cosmetic vehicle in the form of an aqueous suspension of the sol-gel particles, or as a dried sol-gel powder.

The sol-gel microcapsules are prepared by the method disclosed in U.S. patent application Ser. No. 60/097,552, i.e., by a) emulsifying hydrophobic solution comprising sol-gel precursors and at least one ultraviolet absorber in an aqueous solution under high shear forces and b) mixing and stirring the obtained emulsion with a second aqueous solution at a suitably selected pH to obtain the sol-gel microcapsules. The size of the microcapsules so obtained can be controlled to the range 0.01–100 $\mu$, preferably 0.1–101 $\mu$, by selecting suitable reaction conditions.

The sol-gel precursors can be selected from metal or semi-metal alkoxide monomers, or metal ester monomers, or semi-metal ester monomers or monomers of the formula $M(R)_n(P)_m$, wherein M is a metallic or semi metallic element, R is a hydrolyzable substituent, n is an integer from 2 to 6, P is a non polymerizable substituent and m is and integer from 0 to 6, or partially hydrolyzed and partially condensed polymer thereof, or any mixture thereof.

In a preferred embodiment of this invention, the sol-gel microcapsules are silica or organically modified silica microcapsules, produced through the sol-gel process disclosed in U.S. patent application Ser. No. 60/097552. The term "organically modified silica microcapsules" refers to sol-gel microcapsules which are obtained when the sol-gel precursors are of the formula $M(R)_n(P)_m$, wherein M is Si, R is a hydrolyzable substituent, n is an integer from 2 to 5, P is a non polymerizable substituent and m is and integer from 1 to 6.

Since the encapsulation process is general, the capsules may contain various sunscreen compounds or their mixtures.

The hydrophilicity/hydrophobicity character of the capsules is determined by the encapsulating material, and not by the sunscreen compound which is encapsulated inside it. Hence, lypophilic sunscreen compounds, which normally can be dissolved only in hydrophobic, fat containing phases, are easily incorporated in the aqueous phase of any composition, be it o/w (oil in water) or w/o (water in oil) emulsions, or in oil-free compositions, e.g. gels.

The compositions according to the present invention can comprise a hydrophilic composition as the cosmetic vehicle and water dispersible microcapsules encapsulating sunscreen compounds that are hydrophobic, water-insoluble.

The invention further reveals that one or more sunscreen active ingredients are confined within particles of specific particle size, which is independent of the cosmetic vehicle, the composition preparation method, or the sunscreen concentration.

This confinement prevents the rough feel and decreased coverage which are associated with undesired crystallization of sunscreen compounds, since in the event of crystallization the crystals are confined within the capsules, consequently the pleasant feel and efficient coverage are maintained.

The aqueous suspensions of encapsulated sunscreens compounds may contain 1 to 50% wt. sunscreen compounds (a single sunscreen compound, or a combination of several sunscreens compounds together). In a preferred embodiment, the aqueous suspensions contain 20 to 40% wt. sunscreen compounds. The dried sol-gel silica powder may contain 1 to 85% wt. sunscreen compounds. In a preferred embodiment, the dried sol-gel silica powders contain 50 to 80% wt. Sunscreen compound.

The skilled formulator may use a suitable concentration of the aqueous suspension or the powder, to obtain the desired concentration of each sunscreen ingredient in the final composition. Thus, a cosmetic screening composition is obtained, which comprises in a cosmetically acceptable vehicle, about 1 to about 80%, in particular from about 10 to about 50% (w/w of the final composition) water suspension of the sol-gel derived capsules. In the same manner, a cosmetically acceptable screening composition may be obtained, comprising about 1 to about 40%, in particular from about 5 to about 25% (w/w of the final composition) dry powder of sol-gel derived capsules.

The sol-gel containing suspension can easily be combined with o/w compositions at the end of the composition, by simple mixing or stirring with any suitable mixer or stirrer. No steps of heating or high shear force mixing are required in order to achieve good mixing. Nonetheless, the encapsulating material, being inert and stable, can sustain high shear forces such as those active in a homogenizer (Ultra Torax for example) and can sustain heating to 70° C. for the typical time used in composition (up to 60 minutes), without any deterioration in the encapsulation or the capsules properties. Hence, if such processes are required for obtaining the desired formula, the aqueous suspension of the sol-gel derived sunscreen capsules can endure these processes.

If w/o composition is prepared, the aqueous suspension is easily incorporated in the water phase by simple mixing or stirring. The combined water phases can then be handled as desired in a normal composition procedure known to the skilled formulator.

In all these cases, several aqueous suspensions of sol-gel derived capsules containing different sunscreen active ingredients may be added together at any of these stages, in order to obtain formulae that contain several active ingredients in separate capsules, to reduce or even to prevent their cross reactivity.

The sol-gel dried powder can also be easily combined with w/o compositions at the end of the composition, by simple mixing or stirring with any suitable mixer or stirrer. High shear forces may be applied to facilitate fast and efficient mixing of the powder in the cosmetic vehicle. Also, the powder may be re-suspended in the aqueous phase prior to mixing the composition to ease efficient dispersion. The inert nature and stability of the sol-gel derived capsules allows the formulator to utilize these tools without damaging the encapsulation or the capsules properties.

The ease of composition when utilizing the sol-gel derived capsules is a unique advantage of this invention, and is an essential part of the innovation disclosed herein.

Therefore, the composite encapsulated sunscreen active ingredient can be incorporated in cosmetically acceptable oil-in-water or water-in-oil compositions; the final product may take the form of an oil, a gel, a solid stick, a lotion, a cream, a milk, an aerosol, a spray, a powder, a foam, a shampoo, a hair conditioner or lacquer or a make-up. The composite encapsulated sunscreen active ingredient can be added to the cosmetic compositions at the end of the composition process, without the application of heat or shear forces. However, such steps of composition may be carried out if required for the purpose of formulating other constituents of the composition.

It is further demonstrated and emphasized in the case of sunscreen active ingredients, which are solid in nature, or tend to form crystals if the composition is not carefully balanced. Some examples of such active ingredient include benzophenones, dibenzoylmethanes, camphor and phenyl bnezimidazole sulfonic acid in the presence of α and β hydroxy acids. The encapsulation process confines these active ingredients, even in the event of crystallization, within the capsules. Consequently, the problems normally associated with crystals formation, i. e. rough feel and poor coverage, are prevented.

The particle size of the capsules is determined in the encapsulation process, consequently it does not change as a result of the formula or the material encapsulated inside it, even in the event of crystal formation.

An important feature of the capsules is their very efficient encapsulation of the lyophilic sunscreen compounds, which reduces or even prevents their leaching out into aqueous phases and into a large number of cosmetically acceptable oils. Thus, incorporation of incompatible active ingredients when each of them is encapsulated separately in the sol-gel capsules is a very efficient method to reduce or even to prevent their cross reactivity.

Another important objective of this invention is to provide safer sunscreen products. As discussed in the background of this invention, several research groups around the world have demonstrated the potentially harmful effects of several sunscreen products on several in vitro models. It is also recognized that with the increased use of sunscreen product in the world, a growing number of incidents of photoallergy are being reported. In fact, some sunscreen products that are allowed for use by the regulations have been practically withdrawn from the market due to the high number of reported phoroallergy incidents related to them (Schauder and H. Ippen, European UV Sunfilters, Conference Proceedings, Paris 17–18 November 1998, p. 14). With the encapsulated products, the contact between the active sunscreen molecules or its photodegradation products with the human tissue is eliminated. Consequently the harmful potential of the sunscreen active ingredients is dramatically minimized.

It is a further object of this invention to provide a screening composition which reduces or even prevents the penetration by diffusion of sunscreen active ingredient into plastic containers, which may result in fracturing of the packaging material, unacceptable colouring of white packaging material with time, and assay problems.

It has also been found that utilizing the encapsulated sol-gel sunscreen, active ingredients that form crystals in regular compositions can be easily used, as even in the event of crystallization the crystals are confined within the capsule, hence pleasant feel and efficient coverage are maintained.

The sunscreen compound can be selected from the group consisting of 2-ethylhexyl 4-methoxycinnamate, 4-aminobenzoic acid, 2-ethylhexyl-N,N-dimethyl-4-aminobenzoate, 2-cyano-3,3-diphenylacrylic acid 2-ethylhexyl ester (Octocrylene), 2-hydroxy-4-methoxybenzophenone (Oxybenzone) 2-phenylbenzimidizole-5-sulfonic acid, 3,3,5-trimethyl-cyclohexyl-salicilate (Homosalate) octyl salycilate, 4,4'-methoxy-t-butyldibenzoylmethane, 4-isopropyl dibenzoylmethane, 3-(4-methylbenzyledene) camphor, 3-benzylidene camphor, triethanolamine salicylate, 4-N,N-(2-ethylhexyl)methyl aminobenzoic acid ester of 2,4-dihydroxybenzophenone, 4-N,N-(2-ethylhexyl)methyl aminobenzoic acid ester of 4-hydroxydibenzoylmethane, 4-N,N-(2-ethylhexyl)methyl aminobenzoic acid ester of 2-hydroxy-4-(2-hydroxyethoxy) benzophenone, 4-N,N-(2-ethylhexyl)methyl aminobenzoic acid ester of 4-(2-hydroxyethoxy)dibenzoylmethane and mixtures thereof.

A sunscreen composition according to claim 1 wherein the sunscreen active ingredient is in the form of a dried sol-gel powder.

The cosmetic vehicle according to the present invention can be selected from the group consisting of fatty alcohols, fatty acids, fatty acids esters, fatty acid triglycerides, lanolin, natural or synthetic oils and waxes, water in oil and oil in water emulsions.

The sunscreen composition cam further comprise cosmetic adjuvants selected from thickeners, emollients, emulsifiers, humectants, surfactants, film forming agents, preservatives, antifoaming agents, fragrances, lower monoalcoholic polyols, propellants, colorants and pigments.

The sunscreen composition according to the present invention can further contain additives selected from the group consisting of sunscreen actives, sunless tanning actives, skin lightening actives anti-acne actives, anti-skin wrinkling actives, vitamins, nonsteroidal anti-inflammatory actives, anesthetic actives, anti-pruritic actives, antimicrobial actives, and mixes thereof wherein said additives are either dissolved in the cosmetic vehicle or are also in the form of sol-gel microcapsules.

The sunscreen composition according to the present invention can further comprise physical sunblock active ingredients selected from the group consisting of titanium dioxide, zinc oxide, iron oxide, and mixtures thereof wherein said physical sunblock ingredients can be of any commercially available grade, including surface treated particles such as titanium dioxide, which has been surface treated with silica, alumina, stearic acid or mixtures thereof, or any other surface treatment.

The sunscreen composition according to the present invention can further comprises α or β-hydroxy acids such as salycilic acid, glycolic acid, lactic acid, retinoic acid and mixtures thereof.

The present invention further relates to sol-gel microcapsules encapsulating at least one sunscreen compound for use as a sunscreen active ingredient in sunscreen products by easy incorporation into any cosmetically acceptable vehicle without the use of any shear forces.

Following are preferred embodiments for said sol-gel microcapsules:

(a) Sol-gel microcapsules encapsulating 2-ethylhexyl 4-methoxycinnamate, as well as other cinnamate derivatives such as isopentyl 4-methoxycinnamate, diethanolamine methoxycinnamate, 2-ethoxyethyl-4-methoxycinnamate and mixtures thereof.

(b) Sol-gel microcapsules encapsulating Oxybenzone (benzophenone-3), as well as other benzophenone derivatives such as benzophenone-4, benzophenone-8, benzophenone-1, benzophenone-2, benzophenone-5, benzophenone-9 and mixtures thereof.

(c) Sol-gel microcapsules co-encapsulating 2-ethylhexyl p-methoxycinnamate and oxybnezone, as well as as other cinnamate derivatives such as in preferred embodiment (a) and other benzophenone derivatives such as in preferred embodiment (b) and mixtures thereof.

(d) Sol-gel microcapsules co-encapsulating Homosalate and 4,4'-methoxy-t-butyldibenzoylmethane, as well as other derivatives of salicylate such as octyl salycilate, 4-isopropylbenzyl salicylate and dibenzoylmethanes such as isopropyl dibenzoyl methane and mixtures thereof.

(e) Sol-gel microcapsules co-encapsulating Homosalate and 4,4'-methoxy-t-butyldibenzoylmethane and a suitable cosmetic oil such as Capric/caprylic triglyceride, octyl palmitate, C12–C15 alkyl benzoate, dioctyl maleate, propylene glycol dicaprylateldicaprate, diisopropyl adipate, hexyl laurate, and mixtures thereof, as well as other derivatives of salicylate and dibenzoylmethanes such as in claim 21 and mixtures thereof.

(f) Sol-gel microcapsules co-encapsulating 2-cyano-3,3-diphenylacrylic acid 2-ethylhexyl ester (Octocrylene), and 4,4'-methoxy-t-butyldibenzoylmethane, as well as other derivatives of dibenzoylmethane such as isopropyldibenzoylmethane and mixtures thereof.

(g) Sol-gel microcapsules co-encapsulating 2-cyano-3,3-diphenylacrylic acid 2-ethylhexyl ester (Octocrylene) and 4,4'-methoxy-t-butyldibenzoylmethane and a suitable cosmetic oil such as Capric/caprylic triglyceride, octyl palmitate, C12—C15 alkyl benzoate, dioctyl maleate, propylene glycol dicaprylateldicaprate, diisopropyls adipate, hexyl laurate, and mixtures thereof, as well as other derivatives of dibenzoylmethane such as isopropyl dibenzoylmethane and mixtures thereof.

(h) Sol-gel microcapsules co-encapsulating Homosalate and 3-(4-methylbenzyledene) camphor, as well as other derivatives of salicylate such as octyl salicylate, 4-isopropylbenzyl salicylate and other camphor derivatives such as 3-benzylidene camphor and mixtures thereof.

(i) Sol-gel microcapsules co-encapsulating Homosalate and 3-(4-methylbenzyledene) camphor and a suitable cosmetic oil such as Capric/caprylic triglyceride, octyl palmitate, C12-C15 alkyl benzoate, Dioctyl maleate, propylene glycol dicaprylateldicaprate, diisopropyl adipate, hexyl laurate, and mixtures thereof as well as other derivatives of salicylate such as octyl salicylate, 4-isopropylbenzyl salicylate and other camphor derivatives such as 3-benzylidene camphor and mixtures thereof.

(j) Sol-gel microcapsules encapsulating 2-ethylhexyl N,N-dimethyl-p-aminobenzoate, as well as other aminobenzoic acid derivatives such as 4-aminobenzoic acid (PABA), glyceril amionobenzoate, menthyl anthranilate, ethyl PABA, amyl dimethyl PABA and mixtures thereof.

The sunscreen composition according to the present invention can comprise any of the preferred embodiment (a) to (j) or a combination thereof in any acceptable cosmetic vehicle. Following are preferred embodiments of sunscreen compositions according to the present invention:

(k) A sunscreen composition comprising of preferred embodiments (a) and (d) in any acceptable cosmetic vehicle (l) A sunscreen composition comprising of preferred embodiments (a) and (e) in any acceptable cosmetic vehicle (m) A sunscreen composition comprising of preferred embodiments (a) and sol-gel microcapasules encapsulating cinoxate in any acceptable cosmetic vehicle.

The compositions revealed by this invention are of general nature, and the method according to which they are prepared is applicable to any sunscreen compounds currently used, as well as to sunscreen compounds that will be introduced in the future. It is also applicable for other compounds that are regularly used in cosmetic compositions. Furthermore, because of the easy incorporation of the sunscreen active ingredients and the ability to control their hydrophilicity/hydrophobicity character and the capsules size, the cosmetic vehicle to be used with the sunscreen active ingredients is not limited to any group and can be any cosmetically acceptable vehicle.

EXAMPLES

The following examples clarify and demonstrate the invention and are not under any circumstances exclusive. All percentage data is given in weight percentage (w/w) unless specified otherwise.

Example 1

Co-encapsulation Homosalate (IHMS) and Butyl Methoxydibenzoylmethane (BMDBM)

12.85 g BMDBM was dissolved in 38 g HMS. The obtained mixture was dissolved in 51.4 tetraethoxysilane (TEOS) and the organic phase was emulsified in 240 g of aqueous solution containing 1% cetyltrimethyl ammonium chloride (CTAC) under high shear forces using an Ultra-Turrax T-25 basic with S 25 KR-18G dispersing tool (IKA) at 19,000 rpm. The vessel walls were cooled by immersion in an ice-water bath during the homogenizing process. The such obtained emulsion was then poured into an IKA LR-A 1000 Laboratory reactor, equipped with Eurostar Power control-visc P4 stirrer, containing 350 NaOH aqueous solution at pH 11.3. The emulsion was stirred at room temperature for 24 hours. The product was precipitated in a centrifuge at 20,000 g, rinsed by re-suspension in deionized water, precipitated again and finally re-suspended in a 1% polyvinyl pyrrolidon (PVP K30, ISP) to afford a stable dispersion containing 31.3% HMS and 10% BMDBM in the suspension.

The obtained suspension is smooth, pleasant to touch and can be incorporated into various cosmetic vehicles to obtain a sunscreen composition usefull for protecting against ultraviolet radiation.

Example 2

Encapsulation of 2-ethylhexyl p-methoxycinnamate (OMC) in Silica 33 g OMC was dissolved in 33 g TEOS and the organic phase was treated as described in example 1.

The isolated product consisted of an aqueous suspension of silica capsules, containing 35.8% OMC (wiw in final suspension).

The obtained aqueous suspension is smooth, pleasant to touch and can be incorporated into various cosmetic vehicles to obtain a sunscreen composition useful for protecting against ultraviolet radiation.

Example 3

Co-encapsulation of Octocrylene and BMDBM in Silica 4.1 g BMDBM was dissolved in 12.4 g octocaylene. The obtained mixture was dissolved in 49.5 g TEOS and the organic phase treated as described in example 1.

The isolated product consisted of an aqueous suspension of silica capsules, containing 23.5% octocrylene and 7.2% BMDBM (w/w in final suspension).

The obtained aqueous suspension is smooth, pleasant to touch and can be incorporated into various cosmetic vehicles to obtain a sunscreen composition useful for protecting against ultraviolet radiation.

Example 4

Encapsulation of 2-ethylhexyl N,N-dimethyl-p-aminobenzoate (Pad-O) in Silica 16.5 g Pad-O was dissolved in 49.5 g TEOS. The obtained mixture was treated as described in example 1. The isolated product consisted of an aqueous suspension of silica capsules, containing 28.5% Pad-O (w/w in final suspension).

The obtained aqueous suspension is smooth, pleasant to touch and can be incorporated into various cosmetic vehicles to obtain a sunscreen composition useful for protecting against ultraviolet radiation.

Example 5

Encapsulation OMC in Methyl Modified Silica 2.75 g OMC was dissolved in 8.25 g methyltriethoxysilane. The organic phase was emulsified in 50 g of aqueous solution containing 1% ethoxylated sorbitan monooleate (Tween-80, ICI). under high shear forces (as described in example 1). The such obtained emulsion was then poured into 50 g stirred ammonia solution (pH 11.2). The emulsion is stirred at room temperature for 24 hours, followed by stirring at 50° C. for 3 hours. The obtained powder is washed with water and freeze dried to give a fine silica powder containing 24% OMC.

The obtained powder is smooth, pleasant to touch and can be incorporated into various cosmetic vehicles to obtain a sunscreen composition usefull for protecting against ultraviolet radiation.

Examples 6

Oil in Water Composition Containing Hydrophilic Suspension of Apsulated Sunscreen in Silica

| | INCI name | % w/w |
|---|---|---|
| PHASE A | | |
| 1 | Squalane | 5.00 |
| 2 | Cetyl alcohol | 2.50 |
| 3 | Glyceryl stearate & PEG-100 stearate | 5.00 |
| 4 | Propylparabene | 0.10 |
| PHASE B | | |
| 5 | Aqua (water) | 50.20 |
| 6 | Methylparabene | 0.20 |
| 7 | Disodium EDTA | 0.05 |
| 8 | Imidazolidinyl urea | 0.50 |
| PHASE C | | |
| 9 | Methylchloroisothiazolinone & Methylchlorothiazolinone & Benzyl alcohol | 0.05 |

-continued

| | INCI name | % w/w |
|---|---|---|
| PHASE D | | |
| 10 | Silica/OMC/BMDBM (20.6% OMC, 3.8% BMDBM in the water suspension) | 36.40 |

Phase A was heated to 75° C. and mixed. Phase B was heated to 75° C. and mixed. Phase B was poured into phase A and stirred for 5 minutes, followed by 25 minutes homogenization. The mixture was cooled to 55° C., and phase C was added while stirring. The mixture was cooled fbrther to 40° C. and phase D was added while stirring. The cream was stirred for another 5 minutes.

The obtained composition has an estimated SPF of ~10 (preliminary test on 3 volunteers) and is stable, uniform and pleasant to touch.

Examples 7

Oil in Water Composition Containing Hydrophilic Suspension of Apsulated Sunscreen in Silica

| | INCI name | % w/w |
|---|---|---|
| PHASE A | | |
| 1 | Paraffinium liquiduim (minral oil) | 5.00 |
| 2 | Decyl oleate | 5.00 |
| 3 | Dimethicone | 1.00 |
| 4 | Cetearyl alcohol | 1.00 |
| 5 | Glyceryl stearate | 3.00 |
| 6 | Potassium cetyl phosphate | 2.00 |
| PHASE B | | |
| 7 | Aqua (water) | 47.25 |
| 8 | Xanthan gum | 0.15 |
| 9 | Propylene glycol | 5.00 |
| 10 | 2-Bromo-2-nitropropane-1,3 diol & Methylparabne & Phenoxyethanol & Propylbarabne | 0.50 |
| PHASE C | | |
| 11 | Lactic acid 88% (in water) | 0.10 |
| PHASE D | | |
| 11 | Silica/OMC (25% OMC in the water suspension) | 30.00 |

Phase A was heated to 65° C. and mixed. Phase B was heated to 65° C. and mixed. Phase B was cooled, and phase C was added to obtain pH 4.5–4.8. Phase D was stirred into phase B. The combined phase was heated again to 65° C. and phase A was stirred in. The combined mixture was homogenized briefly with a high shear mixer, and the composition was stirred until cooled to room temperature.

The obtained composition is stable, uniform and pleasant to touch. The in vitro SPF value measured for this composition is 10.4.

Examples 8

Water in Oil Composition Containing Hydrophilic Suspension of Encapsulated Sunscreen in Silica

| | INCI name | % w/w |
|---|---|---|
| PHASE A | | |
| 1 | Caprylic/Capric triglyceride | 9.00 |
| 2 | C12-C15 Alkyl benzoate | 7.50 |
| 3 | Diisostearoyl polyglyceryl-3 diisostearate | 3.00 |
| 4 | Hydrogenated castor oil | 0.30 |
| 5 | Cera Alba (Beeswax) | 0.20 |
| PHASE B | | |
| 6 | Aqua (water) | 47.25 |
| 7 | Magnesium sulfate | 1.00 |
| 8 | Glycerin | 1.00 |
| 9 | 2-Bromo-2-nitropropane-1,3 diol & Methylparabne & Phenoxyethanol & Propylbarabne | 0.50 |
| PHASE C | | |
| 11 | Lactic acid 88% (in water) | 0.10 |
| PHASE D | | |
| 12 | Silica/OMC (25% OMC in the water suspension) | 30.00 |

Phase A was heated to 70° C. and stirred. Phase B was heated to 70° C. and stirred. Phase B was cooled, and phase C was added to obtain pH below 5.0. Phase D was stirred into phase B. The combined phase was heated again to 70° C. and phase A was stirred in. The mixture was cooled with stirring, and homogenized at 30° C.

The composition is stable, uniform and pleasant to touch. The in vitro SPF value measured for this composition is 12.8.

Examples 9

Water in Oil Composition Containing Hydrophobic Powder of Encapsulated OMC in Methyl Modified Silica

| | INCI name | % w/w |
|---|---|---|
| PHASE A | | |
| 1 | Caprylic/Capric triglyceride | 9.00 |
| 2 | C12-C15 Alkyl benzoate | 7.50 |
| 3 | Diisostearoyl polyglyceryl-3 diisostearate | 3.00 |
| 4 | Hydrogenated castor oil | 0.30 |
| 5 | Cera Alba (Beeswax) | 0.20 |
| PHASE B | | |
| 6 | Aqua (water) | 65.0 |
| 7 | Magnesium sulfate | 1.00 |
| 8 | Glycerin | 1.00 |
| 9 | 2-Bromo-2-nitropropane-1,3 diol & Methylparabne & Phenoxyethanol & Propylbarabne | 0.50 |
| PHASE C | | |
| 1 | Silica/OMC (60% OMC in the dry powder) | 12.5 |

Phase A was heated to 70° C. and stirred. Phase B was heated to 70° C. and stiffed. Phase C was added to phase A with stirring. All phases were combined together, cooled with stirring and homogenized.

Example 10

Phototoxicity Tests of Encapsulated Sunscreen Compounds Versus Free Sunscreen Compounds The phototoxicity tests are based on the survival of a yeast strain, XD83. A single colony of yeast is inoculated into growth medium, and harvested during the exponential growth. The cells are suspended at a known concentration in a phosphate buffer, to afford a uniform population of cells. The cells are illuminated with simulated sunlight (13 mW/cm$^2$) in the absence or presence of test compounds with continuous stirring. Samples are taken at increasing times (0, 10, 20, 30 minutes of illumination). The samples are analyzed semi-quantitatively, by applying two dilutions of the sample as small droplets (10 μl) to the surface of nutrient agar plates, and incubated at 37° C. for 48 hours. Patches of growth are found around the droplet. It can be easily seen when growth has been decreased. Sunscreen samples are introduces as 1000 μl concentration of the major UVB sunscreen active ingredient. Padimate-O and BMDBM are used as positive controls, both showing a strong phototoxic effect on the growth of the yeast cell. The results are summarized in table 1.

TABLE 1

Phototoxicity test results.

| Sample | Content | Phototoxicity |
|---|---|---|
| Padimate-O | (Positive blank) | Clearly toxic |
| BMDBM | (Positive blank) | More toxic than Padimate-O |
| Light alone | (Blank) | Non-toxic |
| 132(I) | Encapsulated (OMC + BMDBM)$^a$ | Non-toxic |
| 139 | Free (OMC + BMDBM)$^a$ | Toxic about equal to Padimate-O |
| 135 | Blank cream | Slightly toxic |

$^a$7.5% OMC, 1.4 BMDBM.

The results show that encapsulation of the sunscreen active ingredients creates a barrier between the entrapped sunscreen and its photodegradation products and the yeast cells. Consequently, phototxicity is prevented.

Example 11

Plasmid DNA Nicking Tests of Encapsulated Sunscreen Compounds Versus Free Sunscreen Compounds DNA plasmid nicking assay is outlined in Dunford et al, FEBS letts 418, 87–90. The light source consist of a 250-watt ozone free xenon lamp (Spiers Robertson) with a reflector, condensing lens, dichroic mirror to dissipate infrared irradiation and a 2-mm Schott WG 320 filter. The total irradiace between 290 and 400 nm is about 5 mW/cm$^2$.

2.5 μg of supercoiled plasmid DNA in 50 μl of 0.01 M sodium phosphate buffer, pH 7.5, was irradiated in an upturned Eppendorf lid on a brass block embedded in ice and 10 μl samples were taken at each time point and kept on ice. They were analyzed by electrophoresis on neutral 1% agarose gels (1% w/v agarose, 0.5 TBE, 0.3 μg ethidium bromide/ml) run in 0.5 TBE buffer in a GNA 100 or GNA 200 gel tanks (Pharmacia), at 15 V/cm for minigels and 5 v/cm for regular gels, which were stained with ethidium bromide, viewed on a 313 nm UV transilluminator and photographed on a Polaroid 665 positive/negative instant pack film. The number of lesions per molecule of DNA was calculated by measuring the intensity of the supercoiled DNA by densitometry of the agarose gel negative using a model GS-670 imaging densitometer (Bio-Rad). When the total amount of damage inflicted on the DNA is small the amount of undamaged DNA left after an illumination gives a direct measure of the number of strand breaks inflicted. As positive controls Padimate-O and BMDBM are used (at saturation concentrations). It has been shown that both these compounds inflict strand breaks on DNA when they are illuminated in vitro.

The samples, which are o/w emulsions, were added to DNA as suspensions in buffer, so as to arrive as a notional concentration of 1000 μM with respect to the UVB absorbing component. As most sunscreen chemicals are virtually insoluble in water this ensures that they are present at saturation.

FIG. 1 shows that sample 139, in which OMC and BMDBM are present free in the cosmetic composition, significant damage is inflicted on the DNA, similar to the damage inflicted by the BMDBM used as the positive control. Sample 132, in which OMC and BMDBM are encapsulated, does not inflict damage on the DNA, and is similar to plasmid alone, without added chemicals.

It is therefore concluded that encapsulation of sunscreen active ingredients creates a barrier not only for the sunscreens but also to their photodegradation products. This encapsulation reduces and even prevents the adverse reactions found in the free systems, which inflict damage on the DNA.

What is claimed is:

1. A safe and stable sunscreen composition comprising at least one sunscreen active ingredient and a cosmetically acceptable vehicle, wherein said sunscreen active ingredient is in the form of sol-gel microcapsules containing at least one sunscreen compound.

2. A sunscreen composition according to claim 1, wherein the sol-gel microcapsules are prepared by a) emulsifying a hydrophobic solution comprising sol-gel precursors and at least one sunscreen compound in an aqueous solution under high shear forces and b) mixing and stirring the emulsion obtained in step (a) with a second aqueous solution at a suitably selected pH to obtain the sol-gel microcapsules.

3. A sunscreen composition according to claim 2 wherein the sol-gel precursors are metal or semi-metal alkoxide monomers, or metal ester monomers, or semi-metal ester monomers or monomers of the formula $M(R)_n(P)_m$, wherein M is a metallic or semi metallic element, R is a hydrolyzable substituent, n is an integer from 2 to 6, P is a non polymerizable substituent and m is and integer from 0 to 6, or partially hydrolyzed and partially condensed polymer thereof, or any mixture thereof.

4. A sunscreen composition according to claim 1, wherein the sunscreen active ingredient is in the form of an aqueous suspension of the sol-gel microcapsuls.

5. A sunscreen composition according to claim 1, wherein the sunscreen active ingredient is in the form of a dried sol-gel powder.

6. A sunscreen composition according to claim 1, wherein the cosmetically acceptable vehicle is selected from the group consisting of fatty alcohols, fatty acids, fatty acids esters, fatty acid triglycerides, lanolin, natural or synthetic oils and waxes, water in oil and oil in water emulsions.

7. A sunscreen composition according to claim 2, wherein said sol-gel precursors are chosen to impair the sol-gel microcapsules hydophobicity/hydrophilicity character compatible with the cosmetic vehicle of the sunscreen composition in order to obtain a uniform sunscreen composition.

8. A sunscreen composition according to claim 1, wherein the sunscreen compound is any acceptable UVA absorber.

9. A sunscreen composition according to claim 1, wherein the sunscreen compound is any acceptable UVB absorber.

10. A sunscreen composition according to claim 1, wherein the cosmetically acceptable vehicle further contains at least one ultraviolet absorbing compound not enclosed within sol-gel microcapsules.

11. A sunscreen composition according to claim 1, wherein the sol-gel microcapsules are silica or methyl silica or any organically modified silica microcapsules.

12. A sunscreen composition according to claim 1, wherein the cosmetic vehicle is oil-free and wherein the sunscreen compounds are water-insoluble hydrophobic materials and wherein the sol-gel microcapsules are hydrophilic silica microcapsules prepared from silica precursors as sol-gel precursors.

13. A sunscreen composition according to claim 12, in the cosmetically acceptable vehicle is a gel.

14. A sunscreen composition according to claim 1, wherein the cosmetic vehicle comprises an oily or lipophilic phase and wherein the sol-gel microcapsules are hydrophobic microcapsules prepared from organically modified silica precursors.

15. A sunscreen composition according to claim 1, wherein the sunscreen compound in its pure form is a solid and wherein in the event of crystallization, the crystals are confined within said microcapsules thus reducing or preventing the rough feeling and decreased coverage associated with crystallization of sunscreen compounds.

16. A sunscreen composition according to claim 1, further comprising cosmetic adjuvants selected from the group consisting of thickeners, emollients, emulsifiers, humectants, surfactants, film forming agents, preservatives, antifoaming agents, fragrances, lower monoalcoholic polyols, propellants, colorants and pigments.

17. A sunscreen composition according to claim 1, whose final form is oil-in-water or water-in oil compositions; or an oil, or a gel, or a solid stick, or a lotion, or a cream, or a milk, or an aerosol, or a spray, or a powder, or a foam, or a shampoo, a hair conditioner or lacquer or a make-up.

18. A sunscreen composition according to claim 1, comprising about 1 wt.% to about 80wt. %, water suspension of sol-gel derived microcapsules.

19. A sunscreen composition according to claim 1, comprising about 10 wt.% to about 50wt. %, water suspension of sol-gel derived microcapsules.

20. A sunscreen composition according to claim 1, comprising about 1 wt.% to about 40 wt.% of dry powder of sol-gel derived capsules.

21. A sunscreen composition according to claim 1, comprising about 5 wt.% to about 25 wt.% of dry powder of sol-gel derived capsules.

22. A sunscreen composition according to claim 1, wherein the sunscreen compounds are selected from the group consisting of 2-ethylhexyl 4-methoxycinnamate, 4-aminobenzoic acid, 2-ethylhexyl N,N-dimethyl-p-aminobenzoate, 2-cyano-3,3-diphenylacrylic acid 2-ethylhexyl ester (Octocrylene), 2-hydroxy-4-methoxybenzophenone (Oxybenzone), 2-phenylbenzimidizole-5-sulfonic acid, 3,3,5-trimethyl-cyclohexyl-salicylate (Homosalate), octyl salycilate, 4,4'-methoxy-t-butyldibenzoylmethane, 4-isopropyl dibenzoylmethane, 3-(4'-methylbenzyledene) camphor, 3-benzylidene camphor, triethanolamine salicylate, 4-N,N-2-ethylhexyl)methyl aminobenzoic acid ester of 2,4-dihydroxybenzophenone, 4-N,N-(2-ethylhexyl)methyl aminobenzoic acid ester of 4-hydroxydibenzoylmethane, 4-N,N-2-ethylhexyl)methyl aminobenzoic acid ester of 2-hydroxy-4-(2-hydroxyethoxy)

benzophenone, 4-N,N-(2-ethylhexyl)methyl aminobenzoic acid ester of 4-(2-hydroxyethoxy)dibenzoylmethane and mixtures thereof.

23. Sol-gel microcapsules encapsulating at least one sunscreen compound for use as a sunscreen active ingredient in sunscreen products.

24. Sol-gel microcapsules according to claim 23 or use as a sunscreen active ingredient in sunscreen products wherein said sunscreen products are prepared by incorporating said microcapsules into any cosmetically acceptable vehicle without the application of heat or shear forces.

25. Sol-gel microcapsules according to claim 23, encapsulating a sunscreen compound selected from the group consisting of Oxybenzone (benzophenone-3), benzophenone-4, benzophenone-8, benzophenone-1, benzophenone-2, benzophenone-5, benzophenone-9 and mixtures thereof.

26. Sol-gel microcapsules according to claim 23 co-encapsulating Homosalate or any other derivative of salicylate together with 4,4'-methoxy-t-butyldibenzoylmethane and with a suitable cosmetic oil.

27. Sol-gel microcapsules according to claim 26, wherein the cosmetic oil is selected from the group consisting of Capric/caprylic triglyceride, octyl palmitate, C12-C15 alkyl benzoate, dioctyl maleate, propylene glycol dicaprylate/dicaprate, diisopropyls adipate, hexyl laurate.

28. Sol-gel microcapsules according to claim 23, co-encapsulating 2-cyano-3,3-diphenylacrylic acid 2-ethylhexyl ester (octocrylene), together with 4,4'-methoxy-t-butyldibenzoylmethane or 4-isopropyl dibenzoylmethane and mixtures thereof.

29. Sol-gel microcapsules according to claim 28 further co-encapsulating a suitable cosmetic oil.

30. A sunscreen composition according to claim 1, comprising at least two sunscreen active ingredients.

31. A composition according to claim 1, further containing additives selected from the group consisting of sunscreen actives, sunless tanning actives, skin lightening actives anti-acne actives, anti-skin wrinkling actives, vitamins, nonsteroidal anti-inflammatory actives, anesthetic actives, anti-pruritic actives, anti-microbial actives, and mixtures thereof wherein said additives are dissolved in the cosmetic vehicle.

32. A composition according to claim 1, further containing additives selected from the group consisting of sunless tanning actives, skin lightening actives anti-acne actives, anti-skin wrinkling actives, vitamins, nonsteroidal anti-inflammatory actives, anesthetic actives, anti-pruritic actives, anti-microbial actives, and mixtures thereof, wherein at least one of said additives is also in the form of sol-gel derived microcapsules encapsulating said additive.

33. A sunscreen composition according to claim 1, further comprising physical sunblock active ingredients selected from the group consisting of titanium dioxide, zinc oxide, iron oxide, and mixtures thereof.

34. A sunscreen composition according to claim 33, wherein the physical sunblock ingredients are of a commercially available grade, including surface treated particles.

35. A sunscreen composition according to claim 1, further comprising α or β-hydroxy acids.

36. A sunscreen composition according to claim 35 wherein the α or β-hydroxy acids are selected from the group consisting of salycilic acid, glycolic acid, lactic acid, retinoic acid and mixtures thereof.

37. A sunscreen composition according to claim 34, wherein the surface treated particles are titanium dioxide particles which have been surface treated with silica, alumina, stearic acid or by any other surface treatment.

* * * * *